US009649248B2

(12) United States Patent
Lopez et al.

(10) Patent No.: US 9,649,248 B2
(45) Date of Patent: May 16, 2017

(54) STIMULATION ASSEMBLY

(71) Applicants: Eduardo Manuel Lopez, North Miami, FL (US); Dina Monica Cordoba, Vero Beach, FL (US)

(72) Inventors: Eduardo Manuel Lopez, North Miami, FL (US); Dina Monica Cordoba, Vero Beach, FL (US)

( * ) Notice: Subject to any disclaimer, the term of this patent is extended or adjusted under 35 U.S.C. 154(b) by 329 days.

(21) Appl. No.: 14/340,509

(22) Filed: Jul. 24, 2014

(65) Prior Publication Data

US 2015/0141749 A1 May 21, 2015

Related U.S. Application Data

(60) Provisional application No. 61/858,175, filed on Jul. 25, 2013.

(51) Int. Cl.

*A61F 5/00* (2006.01)
*A61H 19/00* (2006.01)
*A47C 15/00* (2006.01)

(52) U.S. Cl.

CPC ........... *A61H 19/40* (2013.01); *A47C 15/008* (2013.01); *A61H 19/32* (2013.01); *A61H 2201/0142* (2013.01); *A61H 2201/0149* (2013.01); *A61H 2201/149* (2013.01); *A61H 2201/1669* (2013.01)

(58) Field of Classification Search

CPC ....... A61H 19/40; A61H 19/50; A47C 15/008
USPC ........................................................ 600/38–41
See application file for complete search history.

(56) References Cited

U.S. PATENT DOCUMENTS 5,385,154 A * 1/1995 Fuhrman .............. A47C 15/008 128/845
6,135,552 A 10/2000 Waguri
6,698,431 B1 * 3/2004 Harris .................. A47C 15/008 128/845
7,524,283 B1 4/2009 Johnstone, II
2003/0075958 A1 4/2003 Yogore et al.
2003/0111876 A1 * 6/2003 Black .................. A47C 15/008 297/179
2006/0004251 A1 * 1/2006 Bookwalter ........... A61H 19/44 600/38

* cited by examiner

*Primary Examiner* — John Lacyk
(74) *Attorney, Agent, or Firm* — Mark Terry

(57) ABSTRACT

An apparatus comprises a base portion comprising an aperture for receiving an organ of a user and a base support member extending downward. The base portion moves along a track. A pivotable and slidable cross member is joined to the base support member. A frame supports the base portion. The frame is joined to the track for moving the base portion relative to the frame. A first support member extends in a downward direction for a first distance. A second support member extends in a downward direction for a second shorter distance. A guide joins ends of the first support member and the second support member. A T-shaped member sliding on the guide is in engagement with the cross member wherein the user engaging the base portion and moving the base portion along the track imparts a lateral movement on the base portion.

20 Claims, 5 Drawing Sheets

STIMULATION ASSEMBLY

CROSS-REFERENCE TO RELATED APPLICATIONS

The present Utility patent application claims priority benefit of the U.S. provisional application for patent Ser. No. 61/858,175 entitled “Stimulation Assembly”, filed on 2013 Jul. 25, under 35 U.S.C. 119(e). The contents of this related provisional application are incorporated herein by reference for all purposes to the extent that such subject matter is not inconsistent herewith or limiting hereof

RELATED CO-PENDING U.S. PATENT APPLICATIONS

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to a stimulation device. More particularly, the invention relates to a sexual stimulation device.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. One such aspect of the prior art shows a sexual intercourse chair fabricated from bent steel tubing, channeled metal, compression springs, and two uniquely shaped upholstered foam seats (primary and sedentary). The primary seat is mounted in plural compression springs and has a back that can incline so that it can accommodate either prone, supine, or sideline positions. By way of educational background, another aspect of the prior art teaches of a rocking chair device with front and rear base plates which are made of a strong and non-flexible material such as band iron and are suspended and connected to a machine base frame and capable of being rocked in the front and rear direction, chairs which are arranged on the respective base plates through support columns and come close to each other, and a rocking device which rocks the chairs simultaneously in the direction of coming close to each other and getting away from each other. Another such aspect of the prior art discloses of a machine consisting of a fixed base and a reciprocating platform which imparts that reciprocating motion to a person lying, kneeling, or sitting upon it. A gear motor mounted in the base of the machine drives an eccentrically mounted cam roller. As the cam roller rotates, it is retained in a channel on the underside of the reciprocating platform. The eccentric rotation of the cam roller is converted to linear motion, causing the platform to move back and forth on rollers.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
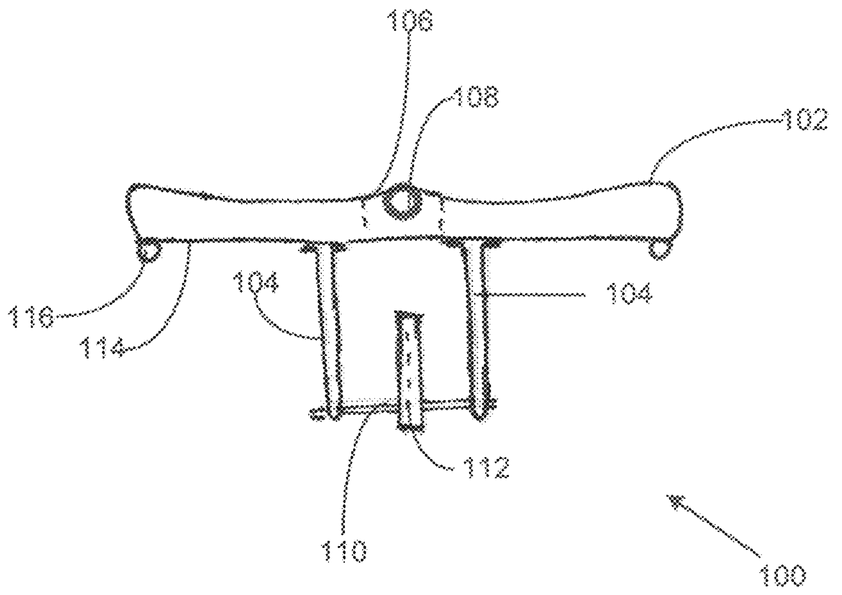
FIG. 1 illustrates a side view of an exemplary stimulation assembly, in accordance with an embodiment of the present invention.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

Headings provided herein are for convenience and are not to be taken as limiting the disclosure in any way.

The enumerated listing of items does not imply that any or all of the items are mutually exclusive, unless expressly specified otherwise.

The terms "a", "an" and "the" mean "one or more", unless expressly specified otherwise.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

There are various types of stimulation assemblies that may be provided by preferred embodiments of the present invention. In one embodiment of the present invention, a stimulation assembly may include a self-powered sexual device configured to be operable for self-stimulation while moving in multiple directions. The stimulation assembly may accommodate a user in various positions, including, without limitation, prone, supine, sitting, and sideline positions. In some embodiments, the assembly may allow for back and forth oscillating motions on a base portion. The base portion, upon which the user may rest, may include a seat having an aperture. The aperture may be adapted to receive an organ, or join with a protruding member for at least partially entering the organ. In some embodiments, the aperture actuates the movement of the assembly upon engagement with the organ. In some embodiments, at least one track may be configured to facilitate motion in a latitudinal and/or a longitudinal path along the frame. A resistance suppression portion located inside each track may help facilitate movement of the track, whereby a power source may not be necessary for the user to move the assembly while engaging the aperture.

In one embodiment of the present invention, the stimulation assembly may include a frame. The frame may provide a structural support, and directional guidance for movements made by the assembly. The frame may be height adjustable to accommodate various sizes of users. In some embodiments, the frame may be folded into storage. A fastener may hold the different members and terminal portions of the frame together. In some embodiments, at least one track may position along a perimeter of the frame. The at least one track may include a channel that is at least partially filled with a resistance suppression portion, such as ball bearings. In some embodiments, at least one guide may join with the frame for helping to guide movements.

In one embodiment of the present invention, a base portion may rest on the frame. The base portion may extend along a longitudinal axis of the frame, providing a surface for the user to rest on, and operate the assembly. The base portion may include a seat for the user to rest one. The seat may be configured to accommodate the user in various positions, including, without limitation, sitting, prone, supine, or sideline positions. The seat may include an aperture. The aperture may be adapted to receive an organ, or join with a protruding member for at least partially entering an organ. In some embodiments, the aperture may actuate the movement capacity of the assembly upon engagement with the organ. In some embodiments, at least one support may extend down from the base portion. The at least one support may be configured to pivot and slide in relation to the base portion. The at least one support may extend from the base portion, joining with a pin that follows, or slides along a guide. The pin may be disposed to form a channel around the guide for facilitated sliding, whereby the base moves in the path of the guide and the at least one track. The pin may slidably move parallel and perpendicular to the frame on the guide to allow for movement of the base in both the horizontal and vertical directions. In some embodiments, at least one leg may extend from the frame towards a ground surface for providing support. Each leg may swing, or extend and retract from the frame to adjust the height of the assembly and provide storage capabilities.

FIG. 1 illustrates a side view of an exemplary stimulation assembly, in accordance with an embodiment of the present invention. In the present embodiment, a stimulation assembly 100 may include a self-powered sexual device configured to be operable for self-stimulation. The stimulation assembly may accommodate a user in various positions, including, without limitation, prone, supine, sitting, and sideline positions. However, in other embodiments, other positions may be utilized. Those skilled in the art, in light of the present teachings, will recognize that these positions provide sexual stimulation when combined with movements in related to a sexual organ. In some embodiments, the assembly may allow for back and forth oscillating motions on a base portion 102. The base portion may include a seat 106 having an aperture 108. The aperture may be adapted to at least partially receive an organ, or join with a protruding member for at least partially entering an organ. The organ may include, without limitation, a penis, a genitalia, and a vagina. In some embodiments, the aperture actuates the movement capacity of the assembly upon engagement with the organ. In one embodiment, a trigger may position within the aperture, whereby when the organ engages the aperture, the trigger releases the movement mechanisms in the frame.

In one embodiment of the present invention, the stimulation assembly may include a frame. The frame may provide a structural support, and directional guidance for movements made by the assembly. The frame may be height adjustable to accommodate various sizes of users. In some embodiments, the frame may be folded into storage. A fastener may hold the different members of the frame together. In some embodiments, at least one track 114 may be configured to facilitate motion in both a latitudinal and a longitudinal path along the frame. A resistance suppression portion 116 located inside guiding tracks help facilitate movement and stimulation, whereby a power source may not be necessary to operate the assembly. The resistance suppression portion may include, without limitation, ball bearings, lubricants, sliding members, and bearings. In some embodiments, at least one guide may join with the frame for helping to guide movements.

In one embodiment of the present invention, a base portion may rest on the frame. The base portion may extend along a longitudinal axis of the frame, providing a surface for the user to rest on, and operate the assembly. The base portion may include a seat for the user to rest one. The stimulation assembly may accommodate a user in various positions, including, without limitation, prone, supine, sitting, and sideline positions. However, in other embodiments, other positions may be utilized. The seat may include an aperture for at least partially receiving the organ. The aperture may be shaped and configured to include, without limitation, a vagina and/or a mouth. The aperture may be adapted to receive the organ, or join with a protruding member that at least partially enters the organ. The protruding member may include, without limitation, a latex penis, a dildo, and a rod member. In some embodiments, the aperture may actuate the movement capacity of the assembly upon engagement with the organ through a mechanism, including, without limitation, a trigger, a lock, a switch, and a friction device.

In one embodiment of the present invention, at least one support may extend down from the base portion. The at least one support may be configured to pivot and slide in relation to the base portion, whereby the base portion moves in conjunction with the at least one support. The at least one support may include a long support and a short support. The at least one support may extend from the base portion, joining with a pin 112 that follows, or slides along a guide 110. The pin may be disposed to at least partially encapsulate the guide for facilitated sliding, whereby the base moves in the path of the guide and the at least one track. In some embodiments, a lubricant may help movement between the pin and the guide. The pin may slidably move parallel and perpendicular to the frame on the guide to allow for movement of the base in both the latitudinal and/or longitudinal path. In one alternative embodiment, the guide may follow a diagonal path, whereby the base may be operable to move diagonally relative to the frame. In some embodiments, at least one leg 104 may extend from the frame towards a ground surface for providing support. Each leg may swing, or extend and retract from the frame to adjust the height of the assembly and provide storage capabilities. Suitable materials for fabricating the at least one leg may include, without limitation, stainless steel, aluminum, polymers, and wood.

Figure 2:
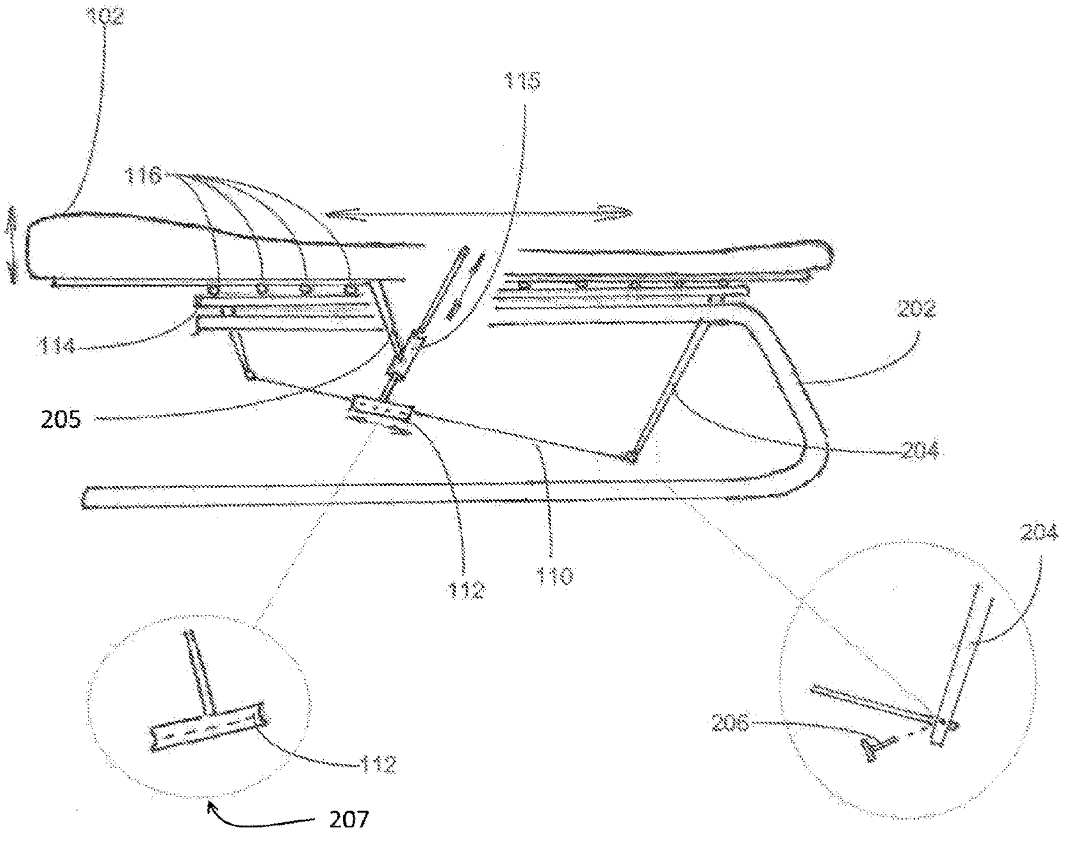
FIG. 2 illustrates a sectioned view of an exemplary stimulation assembly, and blow up views of an exemplary pin and guide, and an exemplary fastener and frame, in accordance with an embodiment of the present invention.

FIG. 2 illustrates a sectioned view of an exemplary stimulation assembly, and blow up views of an exemplary pin and guide, and an exemplary fastener and frame, in accordance with an embodiment of the present invention. In the present embodiment, a frame 202 provides a perimeter support for the base, and also provides a surface to attach each track and each guide and pin. A fastener 206 help join the terminal ends of the frame for enhancing strength, and providing storage capacity during disassembling. The fastener may include, without limitation, a screw, a bolt, a magnet, a weld, and an adhesive. The at least one support 204 may be configured to pivot and slide in relation to a base portion 115. The at least one support may extend from the base portion, joining with a pin 112 that follows, or slides along a guide 110. The pin may be disposed to form a channel around the guide for facilitated sliding, whereby the base moves in the path of the guide and the at least one track. The pin may slidably move parallel and perpendicular to the frame on the guide to allow for movement of the base in both the horizontal and vertical directions. The cross member 205 is joined to the distal end of at least one base support member and is pivotable and slidable with respect to at least one base support member. The T-shaped member 207 is joined to the guide 110 for sliding on the guide 110. The T-shaped member 207 is in engagement with the cross member wherein the user engaging the base portion and moving the base portion along the track imparts lateral movement on the base portion.

Figure 3:
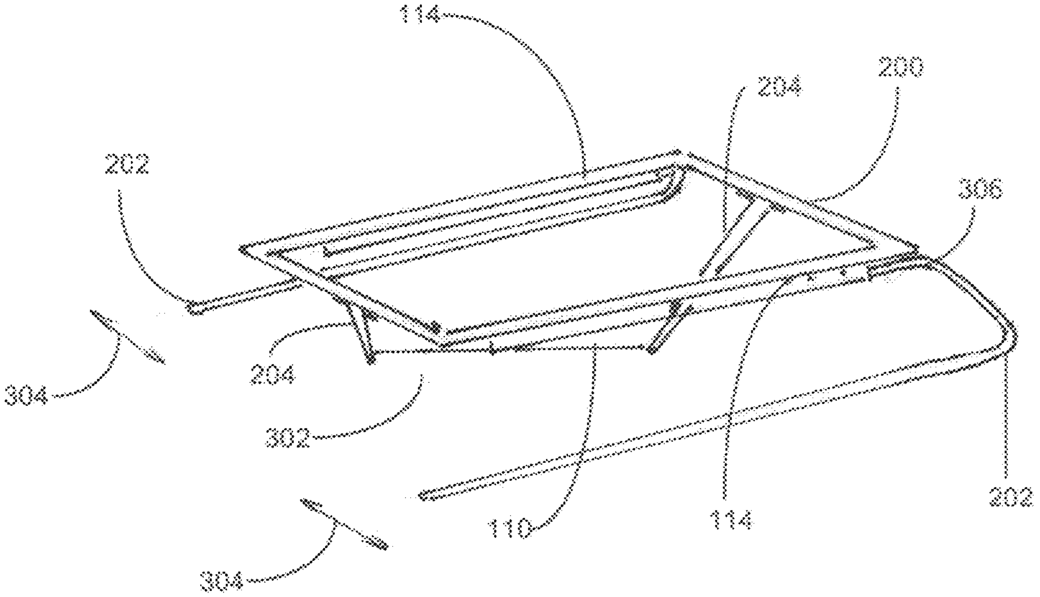
FIG. 3 illustrates a detailed perspective view of an exemplary frame, in accordance with an embodiment of the present invention.

FIG. 3 illustrates a detailed perspective view of an exemplary frame, in accordance with an embodiment of the present invention. In the present embodiment, the frame may be disassembled for storage and cleaning. A fastener may help join the terminal ends of the frame. Suitable materials for the frame may include, without limitation, stainless steel, aluminum, alloys, high density polymers, and wood. In some embodiments, the at least one track and the guide may direct motion in both a latitudinal path, indicated by an arrow 302, and a longitudinal path, indicated by arrows 304, along the frame. In yet another embodiment, the at least one track may allow for a swivel movement 306 disassembling the frame, and providing an additional movement direction during stimulation. In yet another embodiment, the guide may align in a diagonal path for providing yet another direction for movement.

Figure 4:
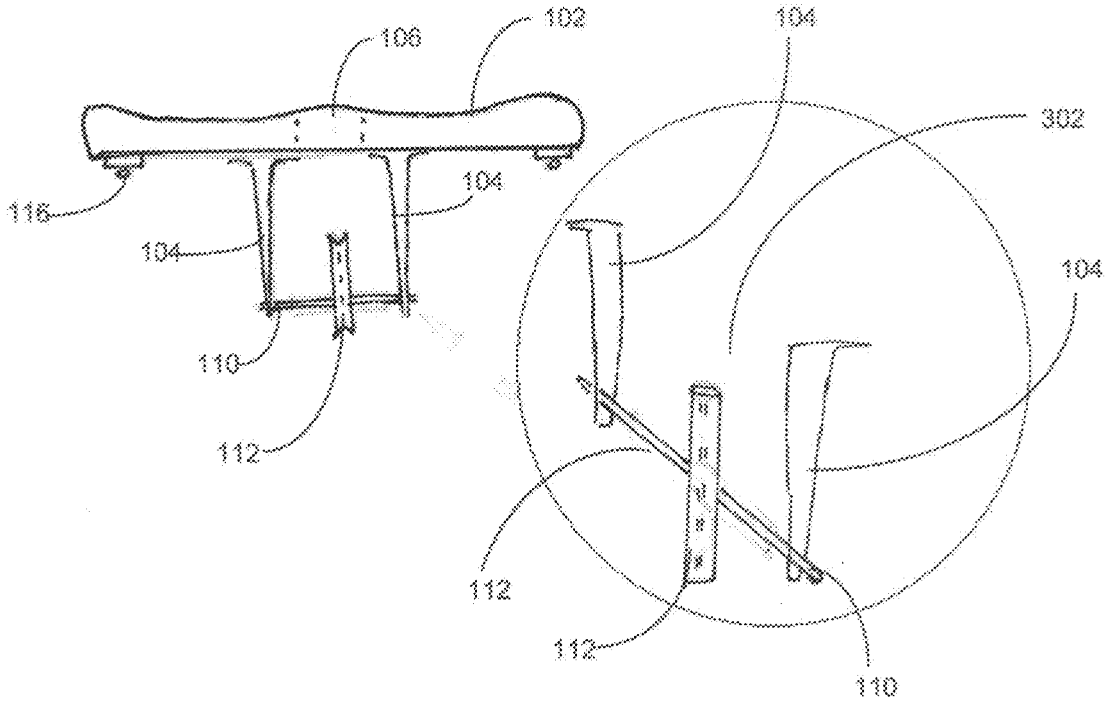
FIG. 4 illustrates a side view of an exemplary stimulation assembly, and a blow up view of an exemplary pin and guide, in accordance with an embodiment of the present invention.

FIG. 4 illustrates a side view of an exemplary stimulation assembly, and a blow up view of an exemplary pin and guide, in accordance with an embodiment of the present invention. In the present embodiment, the pin may at least partially encapsulate the guide for sliding along the latitudinal and/or longitudinal path along the frame. The at least one support may join with the pin to slide the base portion in a desired trajectory and speed. In this manner, the user may have control over the movements of the assembly without requiring an external power source. The guide may include, without limitation, a rigid wire, a metal rod, and a high density polymer rod.

Figure 5:
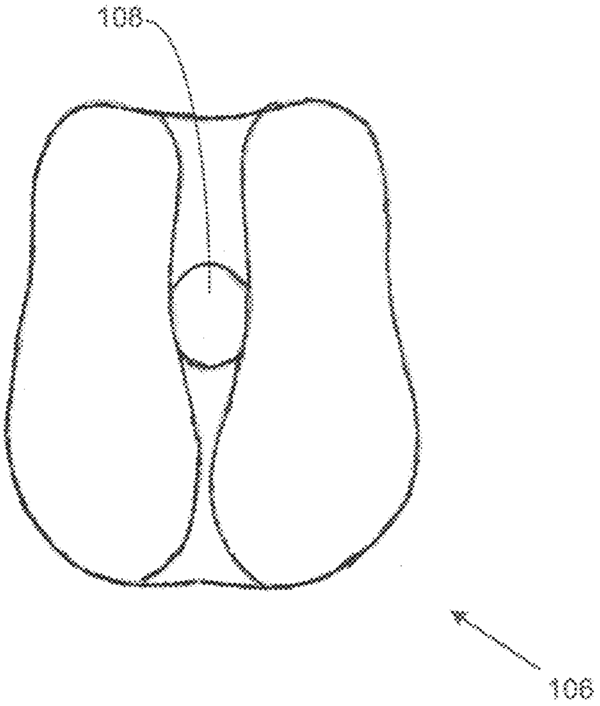
FIG. 5 illustrates a top view of an exemplary seat, in accordance with an embodiment of the present invention.

FIG. 5 illustrates a top view of an exemplary seat, in accordance with an embodiment of the present invention. In the present embodiment, the seat engages the user and an organ. The seat may include stainless steel perimeter portions, and a leather or foam top portion. Those skilled in the art, in light of the present teachings, will recognize that the seat may conform to the shape of buttocks, which are in proximity to the organs. A soft leather portion may engage the fleshy portion of the buttocks, while a rigid metal may provide a perimeter for the aperture. In one embodiment, a male organ may repetitively move within the aperture while the user simultaneously slides in a back and forth motion to enhance the stimulation. In yet another embodiment, a protruding member may extend from the aperture to engage a female organ. The user may repetitively receive the protruding member through the female organ while simultaneously sliding in a back and forth motion to enhance the stimulation.

In one alternative embodiment, the frame may include springs for providing a bouncing affect to the motion for enhanced stimulation. In yet another alternative embodiment, communication devices, such as audio and video machines may provide videos and human sounds for enhanced sexual stimulation. In yet another embodiment, the base portion may accommodate a plurality of users and have a plurality of apertures. In yet another alternative embodiment, each leg may include wheels for providing movement while engaging the assembly.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC §112 (1), all claims must be supported by sufficient disclosure in the present patent specification, and any material known to those skilled in the art need not be explicitly disclosed. However, 35 USC §112 (6) requires that structures corresponding to functional limitations interpreted under 35 USC §112 (6) must be explicitly disclosed in the patent specification. Moreover, the USPTO's Examination policy of initially treating and searching prior art under the broadest interpretation of a "mean for" claim limitation implies that the broadest initial search on 112(6) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC §112 (6) when such corresponding structures are not explicitly disclosed in the foregoing patent specification. Therefore, for any invention element(s)/structure(s) corresponding to functional claim limitation(s), in the below claims interpreted under 35 USC §112 (6), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC §112 (6) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any 3rd parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC §112 (6), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC §112 (6). Applicant(s) note that all the identified documents above which are incorporated by reference to satisfy 35 USC §112 (6) necessarily have a filing and/or publication date prior to that of the instant application, and thus are valid prior documents to incorporated by reference in the instant application.

Having fully described at least one embodiment of the present invention, other equivalent or alternative methods of implementing a sexual stimulation device according to the present invention will be apparent to those skilled in the art. Various aspects of the invention have been described above by way of illustration, and the specific embodiments disclosed are not intended to limit the invention to the particular forms disclosed. The particular implementation of the sexual stimulation device may vary depending upon the particular context or application. By way of example, and not limitation, the sexual stimulation device described in the foregoing were principally directed to a self-powered sexual device configured to be operable for self-stimulation while moving in multiple directions implementations; however, similar techniques may instead be applied to a sexual stimulation device for multiple partners operating the device to more in multiple directions, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims. The following claims are hereby incorporated into the detailed description, with each claim standing on its own as a separate embodiment.

What is claimed is:

1. An apparatus comprising:

a base portion being configured for engaging a user during sexual stimulation, said base portion comprising at least one central aperture being configured for at least partially receiving an organ of the user and at least one base support member extending downward from a bottom;

at least one track unit being joined to said bottom, said at least one track unit being configured for moving said base portion along said at least one track unit;

a cross member being joined to a distal end of said at least one base support member, said cross member being pivotable and slidable with respect to said at least one base support member;

a frame being configured for supporting said base portion, said frame being joined to said at least one track unit for moving said base portion relative to said frame;

a first frame support member being joined to a front of said frame and extending in a downward direction for a first distance;

a second frame support member being joined to a back of said frame and extending in a downward direction for a second distance, said second distance being shorter than said first distance;

a guide being joined to distal ends of said first frame support member and said second frame support member; and a T-shaped member being joined to said guide for sliding on said guide, said T-shaped member in engagement with said cross member wherein the user engaging said base portion and moving said base portion along said track imparts a lateral movement on said base portion.

2. The apparatus as recited in claim 1, further comprising a seat portion being joined to a top of said base portion, said seat portion comprising a buttock type shape and a seat aperture for at least partially engaging an organ of the user.

3. The apparatus as recited in claim 2, in which said seat portion comprises a leather covering.

4. The apparatus as recited in claim 1, in which said central aperture comprises a shape resembling an orifice of a person.

5. The apparatus as recited in claim 1, further comprising at least one leg structure joined to said frame for supporting said frame on a surface.

6. The apparatus as recited in claim 5, in which said at least one leg structure is adjustable in height.

7. The apparatus as recited in claim 1, in which said track unit further comprises a resistance suppression portion for facilitating movement.

8. The apparatus as recited in claim 7, in which said resistance suppression portion comprises ball bearings.

9. The apparatus as recited in claim 1, in which said central aperture is further configured for supporting a phallic shaped member to protrude from said central aperture.

10. The apparatus as recited in claim 1, further comprising a removable pin for joining said cross member to said base support member.

11. The apparatus as recited in claim 1, in which said base support member is pivotable with respect to said base portion for storage.

12. The apparatus as recited in claim 1, further comprising removable pins for joining said guide to said distal ends of the first and second frame support.

13. The apparatus as recited in claim 12, in which said first frame support member and said second frame support member are pivotable with respect to said frame for storage.

14. The apparatus as recited in claim 1, in which said central aperture is further configured to not interfere with movement capacities of the apparatus upon engagement with the user's organ.

15. The apparatus as recited in claim 5, in which said leg structure is pivotable with respect to said frame for storage.

16. An apparatus comprising:

a base portion for engaging a user during sexual stimulation;

means for pivoting and sliding a base with respect to said base portion;

means for supporting said base portion, said supporting means being joined to said moving means for moving said base portion relative to said supporting means;

first means being joined to a front of said supporting means for extending in a downward direction for a first distance;

second means being joined to a back of said supporting means for extending in a downward direction for a second distance, said second distance being shorter than said first distance;

a guide is joined to said first means and said second means; and means being joined to said guiding for sliding on said guiding means for engaging said pivoting and sliding means, wherein the user engaging said base portion and moving said base portion along said moving means imparts a lateral movement on said base portion.

17. The apparatus as recited in claim 16, further comprising means being joined to a top of said base portion for engaging the user.

18. The apparatus as recited in claim 16, further comprising means for supporting said supporting means on a surface.

19. An apparatus comprising:

a base portion being configured for engaging a user during sexual stimulation, said base portion comprising at least one base support member extending downward from a bottom, said at least one base support member being pivotable with respect to said base portion for storage;

a seat portion being joined to a top of said base portion, said seat portion comprising a buttock type shape, a leather covering, and a seat aperture for at least partially engaging an organ of the user, said seat aperture further comprising a shape resembling an orifice of a person, in which said seat aperture is further configured to not interfere with movement capacities of the apparatus upon engagement with the user's organ;

at least one track unit being joined to said bottom, said at least one track unit being configured for moving said base portion along said at least one track unit;

a cross member being joined to a distal end of said at least one base support member, said cross member being pivotable and slidable with respect to said at least one base support member;

a removable pin for joining said cross member to said base support member;

a frame being configured for supporting said base portion, said frame being joined to said at least one track unit for moving said base portion relative to said frame, said tack comprising ball bearings for facilitating movement;

a first frame support member being joined to a front of said frame and extending in a downward direction for a first distance, said first frame support member being pivotable with respect to said frame for storage;

a second frame support member being joined to a back of said frame and extending in a downward direction for a second distance, said second distance being shorter than said first distance, said second frame support member being pivotable with respect to said frame for storage;

at least one leg structure joined to said frame for supporting said frame on a surface, said at least one leg structure being adjustable in height and pivotable with respect to said frame for storage;

a guide being joined to distal ends of said first frame support member and said second frame support member;

removable pins for joining said guide to said distal ends of the first and second frame support; and a T-shaped member being joined to said guide for sliding on said guide, said T-shaped member being in engagement with said cross member wherein the user engaging said base portion and moving said base portion along said track imparts a lateral movement on said base portion.

20. The apparatus as recited in claim 16, in which said seat aperture is further configured for supporting a phallic shaped member to protrude from said seat aperture.

* * * * *